United States Patent [19]
Sereboff

[11] Patent Number: 5,976,098
[45] Date of Patent: Nov. 2, 1999

[54] SUPPORT DEVICE METHOD

[76] Inventor: Joel L. Sereboff, 204 E. Joppa Rd. Penthouse Suite 10, Towson, Md. 21286

[21] Appl. No.: 09/107,882

[22] Filed: Jun. 30, 1998

Related U.S. Application Data

[62] Division of application No. 08/835,784, Apr. 15, 1997, Pat. No. 5,776,088.

[51] Int. Cl.$^6$ .......................................... A61F 5/00
[52] U.S. Cl. ................................................ 602/18
[58] Field of Search .................................. 602/17–19, 32, 602/36; 128/DIG. 23, 96.1, 101.1, 101.2; 2/311, 312, 455

[56] References Cited

U.S. PATENT DOCUMENTS

| | | |
|---|---|---|
| 3,220,406 | 11/1965 | Connelly . |
| 3,308,491 | 3/1967 | Spence . |
| 4,628,913 | 12/1986 | Lerman . |
| 4,761,011 | 8/1988 | Sereboff . |
| 5,027,801 | 7/1991 | Grim . |
| 5,097,824 | 3/1992 | Garth . |
| 5,109,835 | 5/1992 | McDonald et al. . |
| 5,141,489 | 8/1992 | Sereboff . |
| 5,180,361 | 1/1993 | Moore et al. . |
| 5,205,815 | 4/1993 | Saunders . |
| 5,211,623 | 5/1993 | Sarkozi . |
| 5,215,517 | 6/1993 | Stevenson et al. . |
| 5,303,977 | 4/1994 | Sereboff . |

*Primary Examiner*—Jerome W. Donnelly
*Assistant Examiner*—Kim M. Lee
*Attorney, Agent, or Firm*—Diane R. Meyers; Arnold B. Silverman; Eckert Seamans Cherin & Mellott, LLC

[57] ABSTRACT

A support device for supporting and/or immobilizing the articulated or non-articulated areas of an anatomy. The support device comprises a flexible member having connecting ends, intermediate portions, a central portion, a pad member containing a viscous substance in the central portion, and a permanently deformable sheet. The deformable sheet is deformed in situ and is insertable into the central portion adjacent to the pad member and outwardly thereof so that the pad member is positioned toward the anatomy and conforms to the shape of the deformable sheet and provides comfort to the user. Slots are provided in the flexible member for receiving the deformable sheet and for optionally receiving a chin support which in conjunction with an occipital support which is supported by the deformable sheet enables the support device to be used as a cervical brace. The deformable sheet may be a one-piece member or it may be several interconnected curved members, and it may be a simple curve or a compound curve. Associated methods involve deforming the deformable sheet in situ to a desired degree by a medical professional prior to inserting it into the flexible member and prior to or after the support device is secured around the user.

11 Claims, 6 Drawing Sheets

SUPPORT DEVICE METHOD

This application is a divisional application of application Ser. No. 08/835,784, filed Apr. 15, 1997 now U.S. Pat. No. 5,776,088.

BACKGROUND OF THE INVENTION

1. Field of the Invention

This invention relates to a support device for the anatomy and associated method of fitting the support device to an articulated or non-articulated region of a patient and is particularly concerned with a support device construction and associated method which allows the device to be deformed in situ to accommodate a specific need of the patient or user.

2. Background of the Invention

Prior art braces assume various forms and are used to immobilize the articulated regions or joints, such as the spine, finger, knee, ankle or wrist. Such devices are well-known in the art. Cervical collars are used for treating conditions of the neck and cervical spine. Examples of cervical collars are disclosed in U.S. Pat. Nos. 5,097,824; 5,180,361; and 5,215,517, which involve constructions which circumscribe the neck. These devices may primarily be shaped to support the chin and occipital areas and may be of a complicated, rigid or semi-rigid construction.

Another cervical collar design which in addition to circumscribing the neck, provides insertable chin and occipital supports is disclosed in U.S. Pat. No. 3,220,406. These chin and occipital supports are mounted on posts and have a pad support member with a metallic core encased within a compressible foam which permits the pad to be shaped to the head configuration of the patient or user.

A further device disclosed in U.S. Pat. No. 5,141,489 issued to the present inventor entails a cervical brace having chin and head supports which include a pad member which may be a resilient pouch containing a fluid composition which may be of a gel-like viscosity. These pad members allow for deformation thereof upon loads being applied by the chin and the back of the neck to lessen discomfort of the user. Additionally, these chin and head supports are rigidly affixed to the plate members.

A device of U.S. Pat. No. 5,109,835 discloses a complicated headgear for a cervical traction system.

Most, if not all, of these cervical collars and braces of the prior art may employ rigid or semi-rigid integral members whose shape or contour is fixed. Some of these devices are so rigid that they are uncomfortable, or they are so soft that they do not maintain a fixed posture desired by a physician or a medical professional. Furthermore, most of the brace devices are prescribed by the physician in the medical office and fitted to the patient "off site", running the risk of improper fit.

The device of the aforementioned U.S. Pat. No. 5,141,489 employs a pad member which may be of a fluid or gel-like composition. Other fluid or gel-like pads or cushions not particularly used in medical devices as such, but used for the treatment and/or protection of human patients are disclosed in U.S. Pat. Nos. 3,308,491; 4,761,011; and 5,303,977.

Despite these prior art devices, there remains a very real and substantial need for a simple design for a support device which is comfortable, which is easily adaptable as either a brace or as a cervical collar, and which can be selectively deformed into a multitude of shapes in situ by a medical professional to comfortably accommodate a specific postural need of a patient or user.

There remains also a need for a comfortable support device which can be deformed in situ and which can be positioned around a non-articulated area or an articulated area of the anatomy of the animal kingdom.

SUMMARY OF THE INVENTION

The present invention has met the above-described needs. It employs a support device which may be used for immobilizing and/or supporting an articulated area or joint of the anatomy, which may be the human anatomy and which articulated area may be an elbow, a wrist, a knee, or a spine which includes the cervical spine or for supporting a non-articulated area of the human anatomy, such as the forearm or calf. In general, the device is composed of a flexible member with a central portion, intermediate portions, and connecting end portions. The central portion retains a viscous substance, and receives and supports adjustable deformable sheet means to which the viscous substance deforms and which provides optimum support and comfort to the user. The viscous substance acts as a padding for the device. The central portion may preferably consist of an inner and an outer layer of material which may be made of an elastomeric film. The intermediate portions are attached to the central portion and may be made of a soft, breathable fabric. The connecting end portions have distal ends with fastening means. The inner and outer layers of material of the central portion may form central slot means for insertion of the viscous substance and the deformable sheet means. Preferably, the deformable sheet means retains its deformed configuration once it is preformed and is preformed to a desirable degree by a medical professional prior to the deformable sheet means being inserted into the central slot means. The deformable sheet means may comprise a plurality of interconnecting curved members which may be simple or compound curves and which are connected together through tongue and groove means. These curved members are preferably rigid, molded pieces made of hard plastic, metal or aluminum. The deformable sheet means may comprise a one-piece member made of a malleable plastic or metal sheet material which becomes deformable or moldable when placed into hot sand and thereafter shaped by the hand into a desired configuration. Or the deformable sheet means may comprise a one-piece member made of a malleable material such as metal which is easily shaped or formed by pliers, a hammer, or by pressure.

When the support device is placed around an extremity of the anatomy, the deformable sheet means, preferably already in its required degree of deformity, is inserted into the central slot means adjacent to the viscous substance, which viscous substance then presses against the user.

The support device may be used around the neck as a cervical collar and optionally can be used as a cervical brace. If the support device is used as a cervical brace, additional slot means may be provided on at least one of the connecting ends for optionally receiving a chin support member and the deformable sheet means is structured to receive and support an occipital support member. The chin and occipital support members are structured to be easily removed and inserted into the support device and their length may vary in order to be consistent with and to stabilize the postural adjustment of the deformable sheet means. The chin and occipital supports may contain a pad member with a viscous substance. The viscous substance in the flexible member and in the pad member of the chin and occipital supports may be of a gel-filled or fluid-filled composition.

It is, therefore, an object of the present invention to provide an adjustable support device which provides optimum comfort and support to the user.

It is a further object of the present invention to provide a support device which is simple in construction and which is deformable in situ by a medical professional to accommodate a specific postural need of a user.

It is a further object of the present invention to provide a support device with a flexible member comprising a viscous substance and deformable sheet means insertable into the flexible member to displace the viscous substance to conform to the shape of the deformable sheet means, thereby obtaining an optimum fixed support of a non-articulated area or of an articulated area and optimum comfort to the user specific to a medically beneficial posture.

A still further object of the present invention is to provide a support device comprising permanently deformable sheet means and means for optionally and easily inserting chin and/or an occipital support members into the support device for use of the support device as a cervical collar or brace.

A still further object of the present invention is to provide a support device and an associated method which can easily be employable on most articulated areas or joints of the anatomy of the animal kingdom to immobilize these articulated areas or joints, thereby resisting movement thereof, and which provides optimum support and comfort to the user.

A still further object of the present invention is to provide a support device for either a non-articulated area or for an articulated area of the anatomy of the animal kingdom which includes a permanently deformable sheet means which is custom deformed by a physician in his or her office either prior to or after the support device has been positioned around the anatomy of the user.

A still further object of the present invention is to provide a support device for use around an articulated or non-articulated area of a user which device includes a fluid or gel composition and permanently deformable means which dictates the deformability of the fluid or gel composition and the amount of pressure applied to the muscle and/or bone of the articulated or non-articulated area.

Yet a further object of the present invention is to provide a support device which can easily be used on a non-articulated area of a user, such as around the muscle part of the upper and/or lower arm or leg in order to apply pressure thereto to alleviate pain or soreness therein, and which device employs a fluid or gel composition and permanently deformable sheet means.

More particularly, the support device of the present invention may be used on the forearm to treat such conditions as tennis elbow or spasms of the forearm muscles or in emergency situations, the support device of the present invention may be used as a temporary splint or cast, and can be adjustable to the extent that the deformable means can be rebent or redeform once any swelling subsides. For strains, the support device of the present invention can be used in lieu of a tensor bandage.

These and other objects of the present invention will be fully understood and appreciated from the following description of the invention upon reference to the illustrations appended thereto.

DESCRIPTION OF THE PREFERRED EMBODIMENTS

An articulated area is herein defined as being a joint of the anatomy of the animal kingdom. For example, for a human being, this joint may be an elbow, a knee, or a neck. A non-articulated area is herein defined as being more of a muscular part of the anatomy of the animal kingdom. For example, for a human being, a non-articulated area may be a forearm or a calf. An area of a user is defined herein as being either an articulated area or a non-articulated area.

The present invention is secured around an articulated area or a non-articulated area of an extremity of a patient or user and is employed on the anatomy of the animal kingdom which may be a human being or other members of the animal kingdom, such as a racehorse, and is preferably applied in situ on the extremity by a medical professional, such as a physician, an orthopedist, a veterinarian, or any other trained medical person.

Figures 1, 2:
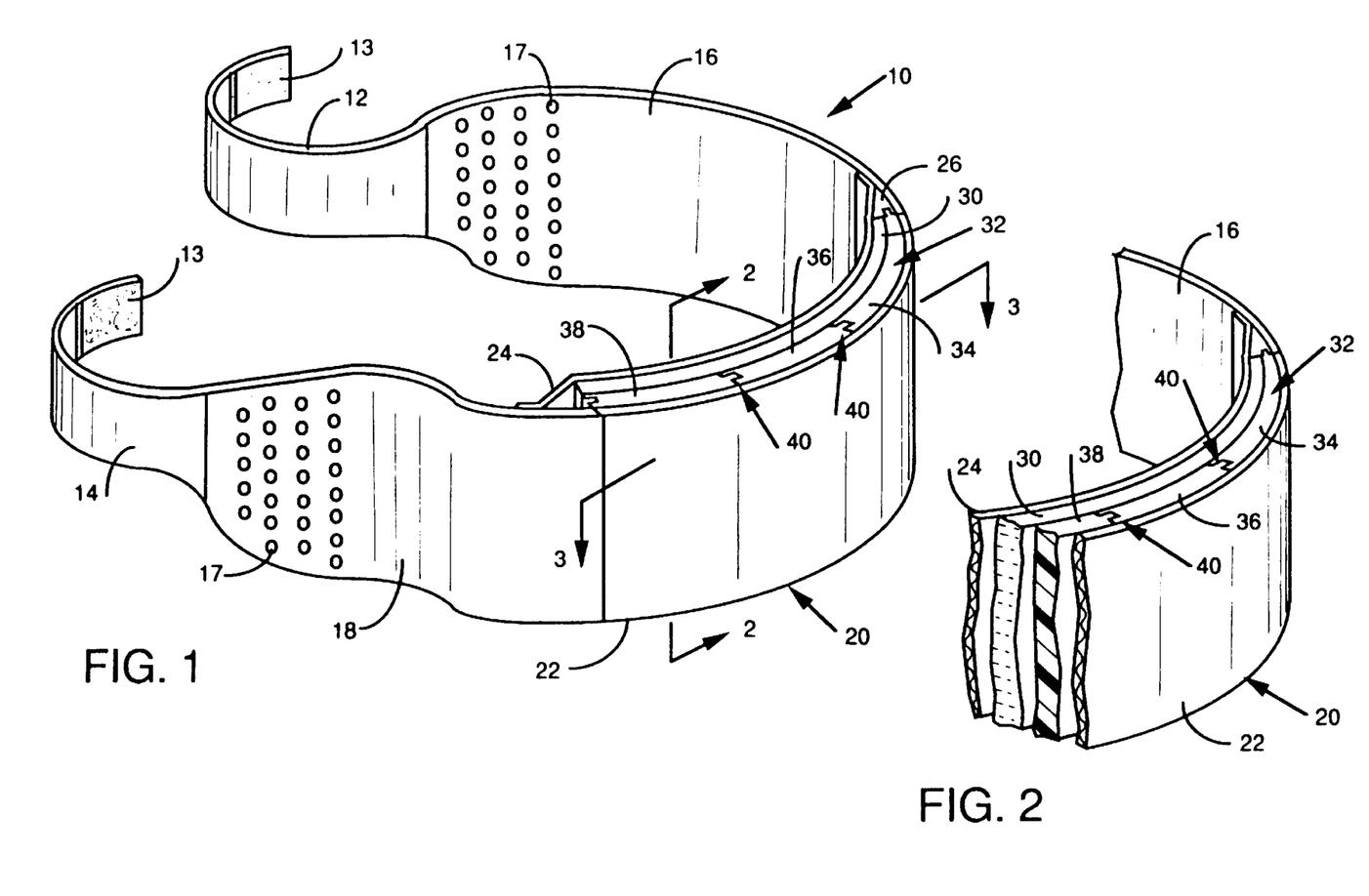
FIG. 1 is a schematic, perspective view of a support device of the present invention.
FIG. 2 is a cross-sectional view taken along lines 2—2 of FIG. 1 and partly broken away.
Figures 3, 4, 5:
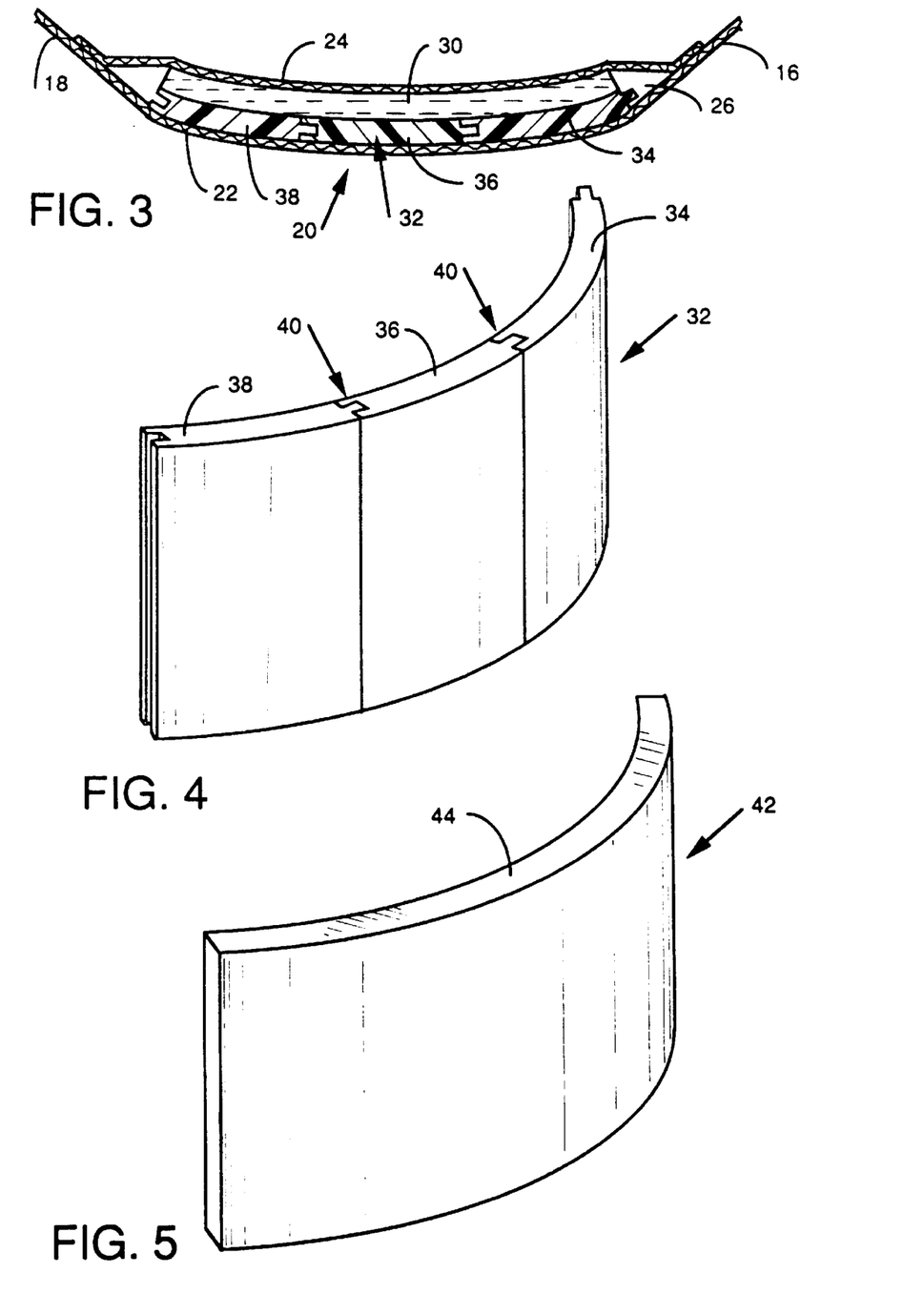
FIG. 3 is a cross-sectional view taken along lines 3—3 of FIG. 1.
FIG. 4 is a perspective view of a first embodiment of the deformable means of the present invention.
FIG. 5 is a perspective view of a second embodiment of the deformable means of the present invention.

Referring first to FIGS. 1, 2, and 3 there is shown in accordance with the present invention, a support device generally indicated by numeral 10.

Support device 10 comprises a flexible member which is comprised of connecting ends 12 and 14, intermediate portions 16 and 18, and a central portion 20, and which tapers from central portion 20 down to connecting ends 12 and 14. Central portion 20 is comprised of an outer layer of material indicated at 22 and an inner layer of material indicated at 24. Preferably, outer layer 22 and inner layer 24 are made of a flexible material such as an elastomeric film or a material selected from the group consisting of, for example, urethane, polyethylene, or a plastic film bonded to fabric, and may be attached to each other at least along their longitudinal edges of central portion 20 through means such as bonding or stitches to form an encasement or slot 26 therebetween for receiving a pad member 30 which extends at least along the length of central portion 20.

Intermediate portions 16 and 18 are, preferably, made of a soft, breathable natural or synthetic fabric, which material is selected from the group consisting of, for example, cotton, wool, or nylon, and are connected to ends 12 and 14 and central portion 20 through suitable means such as through bonding or stitching. This breathable type of material for intermediate portions 16 and 18 is represented by the several circles appearing therein, some of which circles are indicated at numeral 17. The distal portion of each end 12 and 14 contains fastening means, such as hook and loop fasteners 13, commonly known as Velcro®, so that when ends 12 and 14 are overlapped they are securely fastened together to releasably secure support device 10 around the extremity of a user.

Pad member 30 is, preferably, resilient and, preferably, is a fluidly sealed resilient pouch containing a substantially fluid composition of a relatively high viscous substance with an ultra-low density, such as a variety of gel compositions. This type of pad member 30 allows for deformation thereof and the distribution of loading forces being applied by the extremity of the user over a wide area and thus provides for less discomforture because of the diminished pressure on the part of the user when the user is in prolonged contiguous interfacing contact with the support device 10 employing the essence of the invention as fully explained hereinbelow.

The type of pad member 30 which may be employed in the present invention is disclosed in the aforementioned U.S. Pat. No. 5,141,489 which issued to the present inventor, and which is incorporated herein by reference.

Still referring to FIGS. 1, 2, and 3, essentially the present invention involves a deformable sheet means 32 which is insertable between outer layer 22 and pad member 30 in slot 26 of central portion 20.

As shown in FIG. 4, the deformable sheet means 32 comprises curved members 34, 36, and 38 which are interconnected together by tongue and groove means 40 in a concave configuration. Preferably, curved members 34, 36, and 38 are made of a rigid, hard material selected from the group consisting of plastic, metal or aluminum. Curved members 34, 36, and 38 preferably are molded pieces having a predetermined curvature such that when they are pieced together in situ by the medical professional, they comfortably accommodate a specific postural need of a patient or user. All or some of curved members 34–38 may be used depending on the required length for deformable means 32. If needed, additional curved members similar to curved members 34, 36, and 38 may be provided in order to increase the length of deformable sheet means 32. The dimensions of curved members 32, 34, 36 may vary, but preferably their curvature is such that when curved members 32, 34, 36 are joined together they form a continuous curve. Curved members 32, 34, 36 of FIGS. 1, 2, 3, 4, 6, 7, and 9 are simple curved members and when connected together they form one continuous curve in one direction, however, it is to be appreciated that these curved members 32, 34, and 36 may be compound curved members in that they may contain several curves extending in several directions.

FIG. 5 illustrates a further embodiment for a deformable sheet means 42 which may be used in the support device 10 of FIGS. 1–3 instead of deformable sheet means 32 of FIG. 4. Deformable sheet means 42 of FIG. 5 comprises an integral one-piece member 44 which may be made of a soft plastic or of a thin malleable material which is easily shaped and deformed, such as metal, for example, steel, aluminum, or like composition. If deformable sheet 42 is metal, then it may be bent by a pair of pliers, a hammer, or by other means of pressure. If deformable sheet 44 is made of a soft plastic material, it can become moldable when placed into hot sand and thereafter shaped by hand into a desired configuration. Deformable sheet means 42 of FIG. 5 is shown as being a simple curved member in a concave configuration and in one direction. However, it is to be understood that it can be formed into any desirable shape and it can be a complex curved member in that it curves in more than one direction. There may be instances where the medical professional may desire to remove deformable sheet means 42 of FIG. 5 to rebend it by proper means explained hereinabove in order to adjust support device 10 to any diminished swelling or soft tissue or postural changes which may occur. The term "permanently" as employed herein, with respect to the deformation sheet means, shall refer to these types of deformation as distinguished from resilient deformation.

The support device 10 of FIGS. 1–3 employing the deformable sheet means 32 or 42 of FIGS. 4 and 5, respectively, may be used on an articulated or on a non-articulated area of a patient or user. If used on an articulated area of the human anatomy such as an elbow, wrist, or knee, then support device 10 acts as a brace to immobilize or resist movement of the joint while applying support thereto and, thus, helping to alleviate pain or soreness during the healing process. If support device 10 is used on a non-articulated area of the human body such as around the forearm or calf of a human being, then support device 10 acts to support and stabilize a muscle and thus help alleviate pain or soreness in this area during the healing process.

Figure 6:
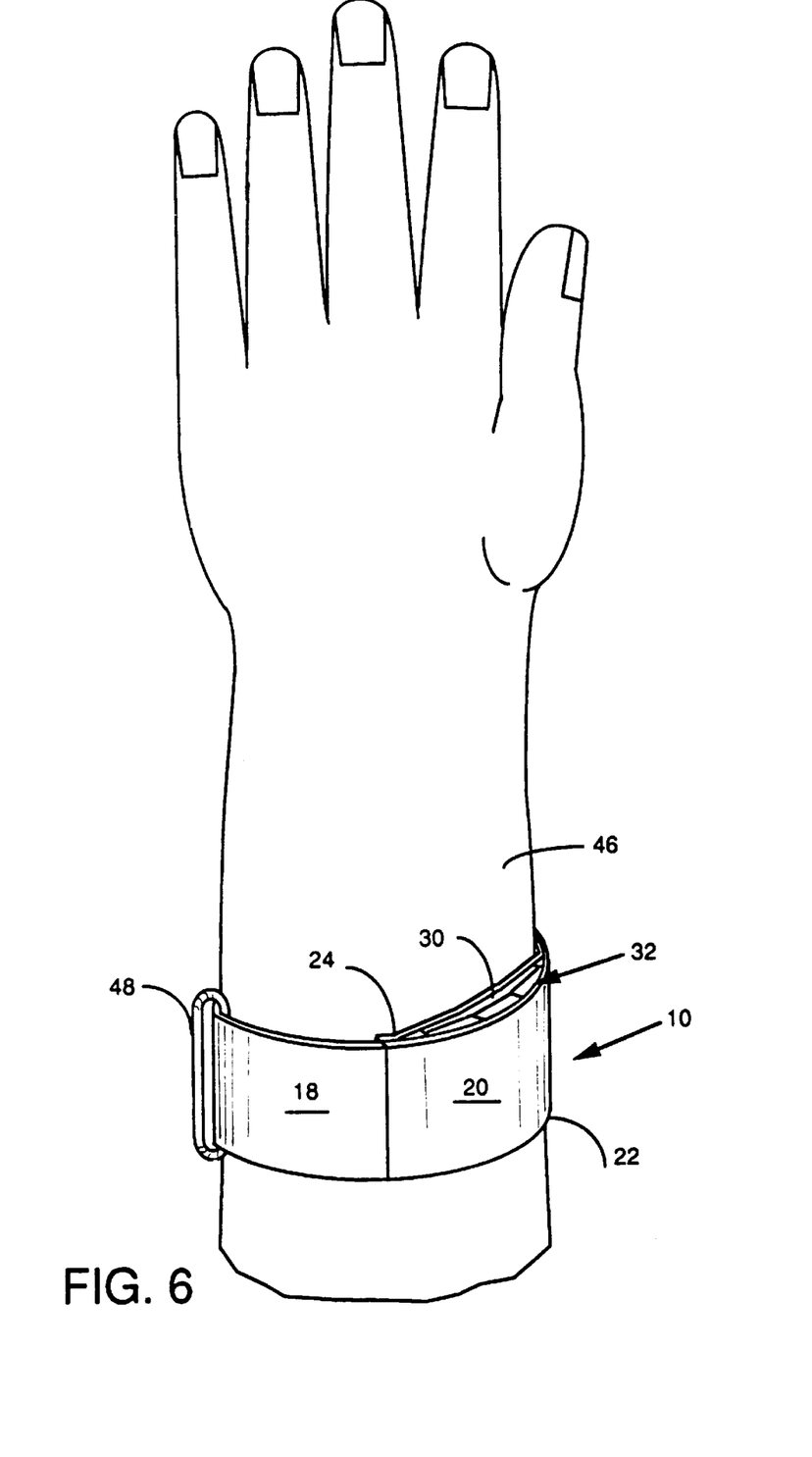
FIG. 6 is a perspective view of the support device of the present invention as mounted around a forearm of a patient or user.

For exemplary purposes, FIG. 6 shows support device 10 of FIGS. 1–3 as being secured around the forearm 46 of a human being to give support thereto. Support device 10 provides a loop 48, which may be made of plastic on 14 so that end 12 can be looped therethrough and overlapped with itself in a well-known manner for securement of support device 10 on forearm 46. For this purpose, Velcro® or snaps may be provided on the appropriate surfaces of connecting ends 12, 14, or intermediate portions 16, 18.

In use, support device 10 is secured in situ by a medical professional in his or her office on either an articulated or on a non-articulated area of a patient or user such that inner layer 24 of central portion 20 lays against the area with pad member 30 being adjacent to inner layer 24. If deformable sheet means 32 of FIG. 4 is used, then the required number of curved members 34, 36, 38 are snapped together and inserted into slot 26 of central portion 20 between pad member 30 and outer layer 22. If deformable sheet means 42 of FIG. 5 is used, then it is custom bent as discussed hereinabove to a predetermined degree and into a desired configuration by the medical professional and inserted into slot 26 in a manner similar to that explained with reference to deformable sheet means 32. This insertion of deformable means 32 or 42 into slot 26 deforms pad member 30 to displace the gel or fluid composition in pad member 30. This arrangement of the pad member 30 immediately adjacent to the area of the user and the permanently deformed deformable sheet means 32 or 42 against the pad member 30 dictates the amount of alteration which is to be made to the muscle or joint and still provide optimum comfort to the user.

It is to be appreciated that in certain instances the deformable sheet means 32, 42 may be formed in its desired configuration and inserted into slot 26 between pad member 30 and outer layer 22 prior to support device being secured to an articulated or a non-articulated area of a user.

Figure 7:
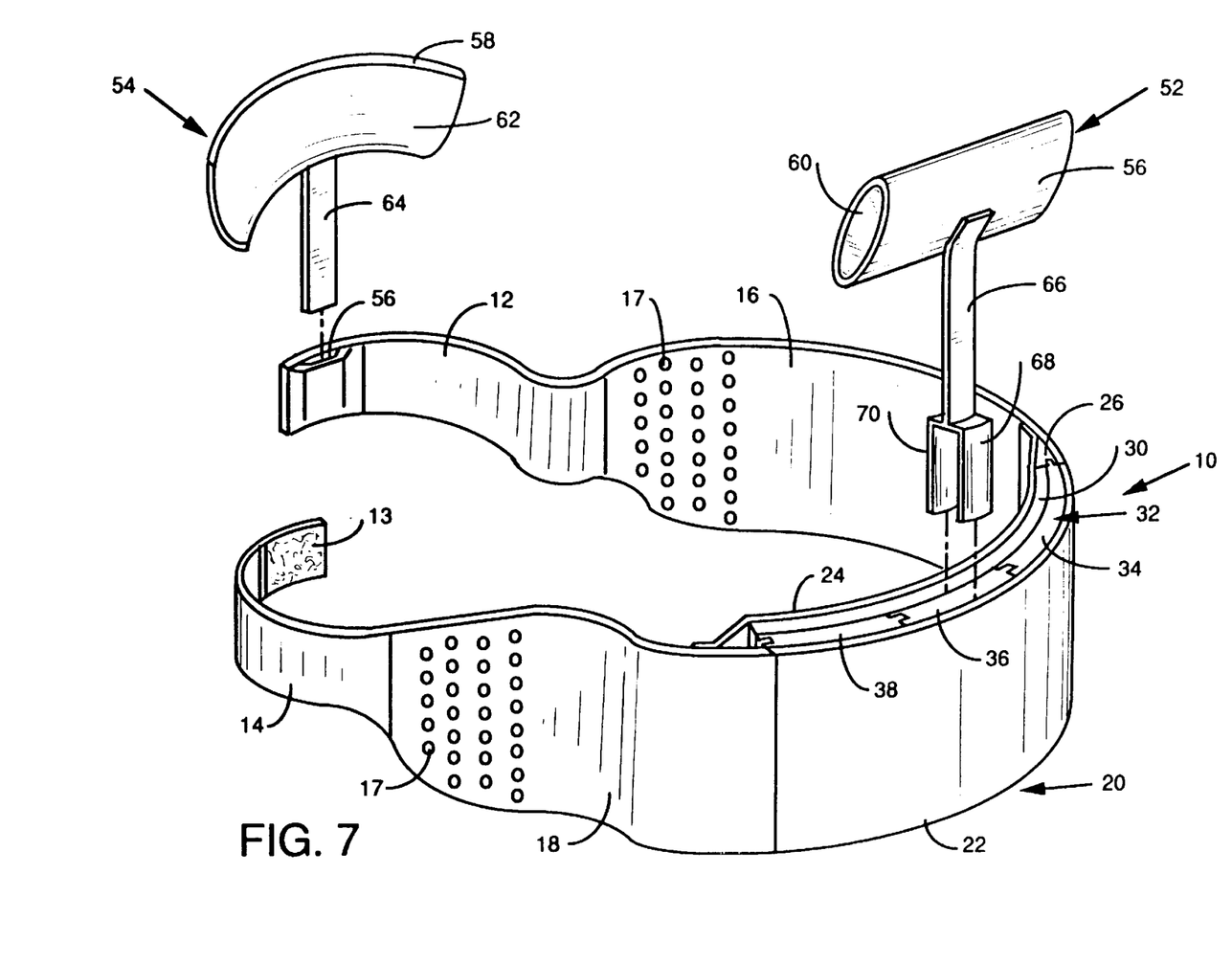
FIG. 7 is an exploded, perspective view of the support device of the present invention incorporating chin and occipital supports for use as a cervical brace.
Figure 8:
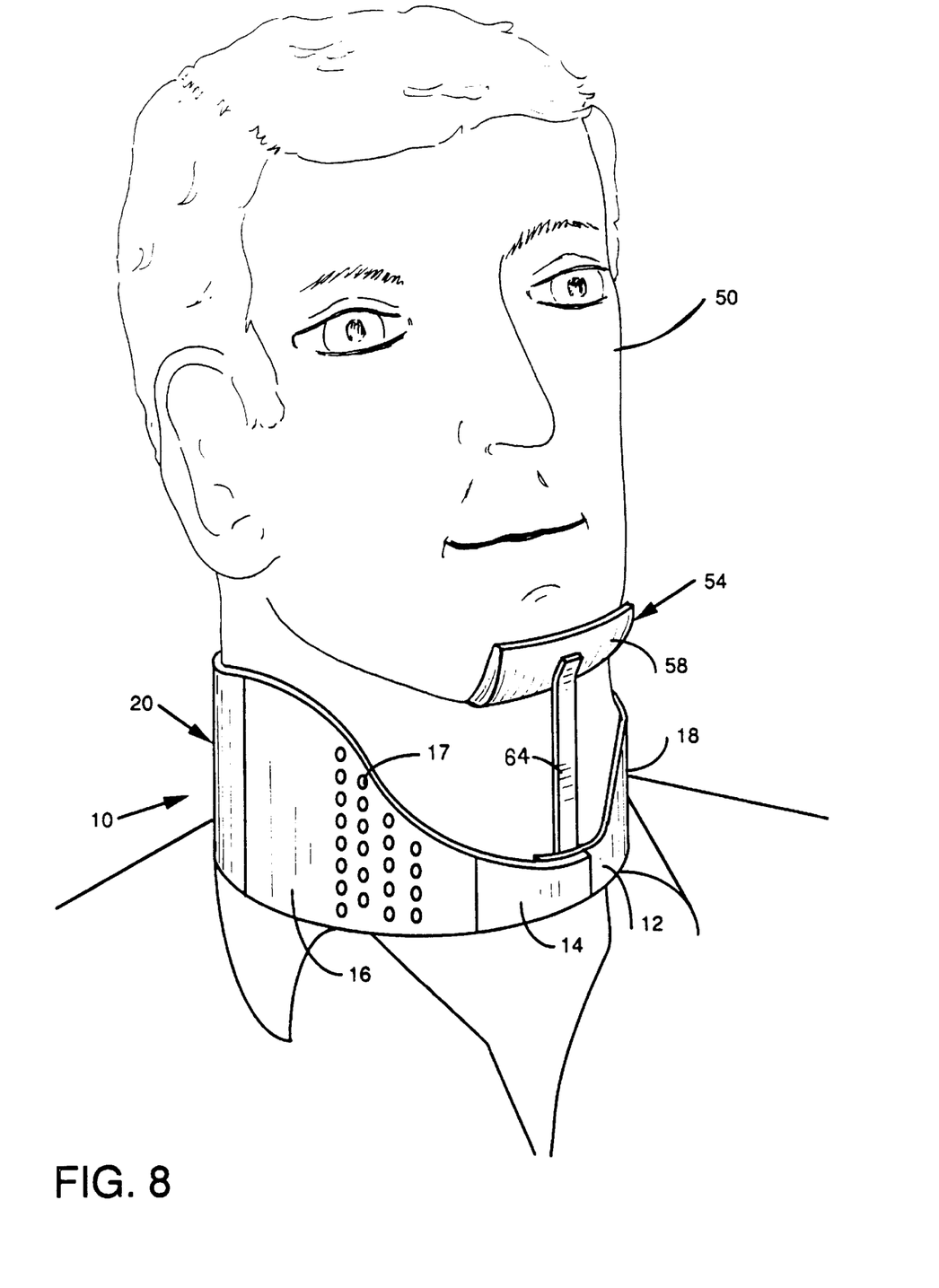
FIG. 8 is a right front, perspective view of the support device of FIG. 7 as mounted around the neck of a patient or user.
Figure 9:
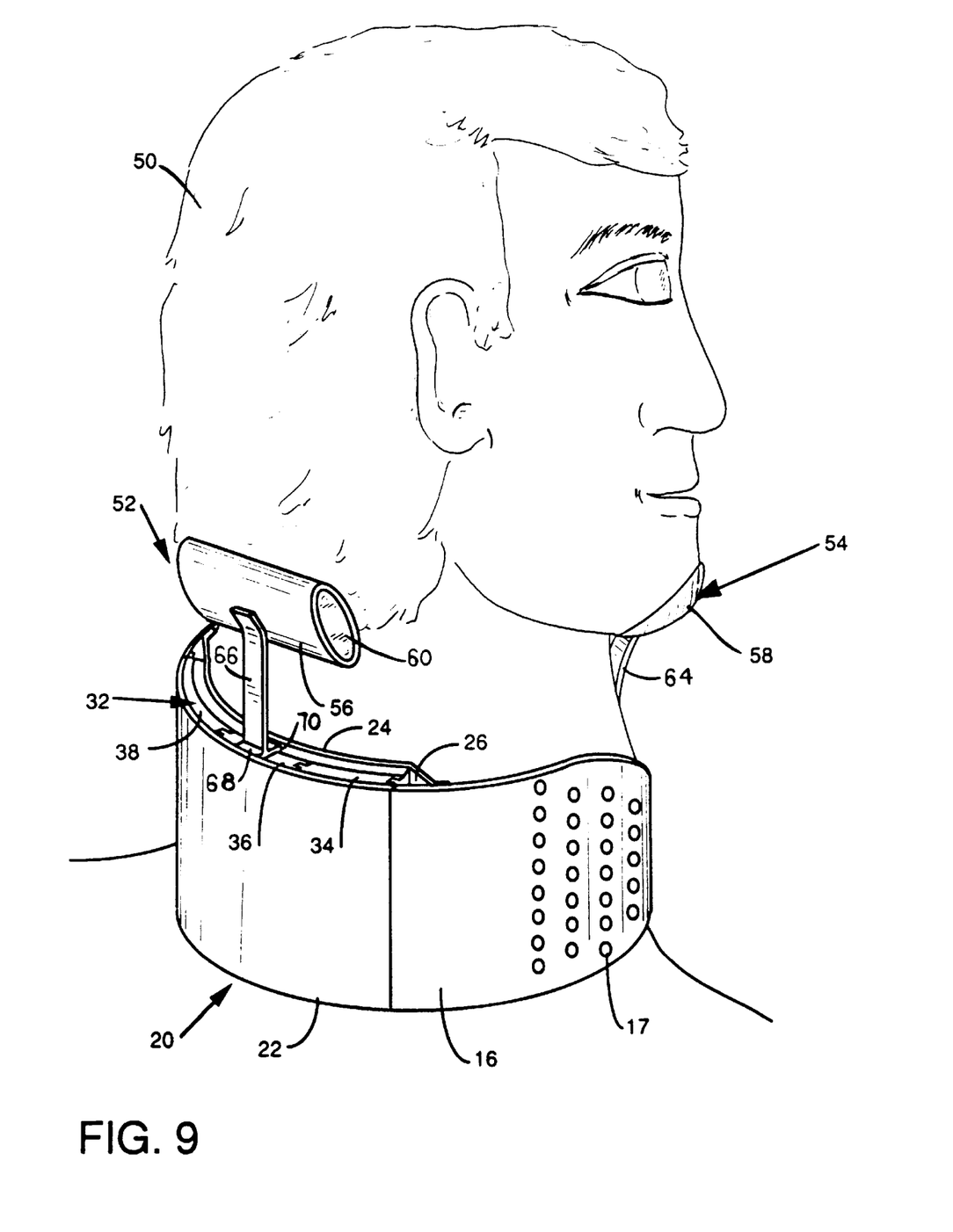
FIG. 9 is a right rear, perspective view of the support device of FIG. 7 as mounted around the neck of a patient or user.

FIGS. 7, 8 and 9 illustrate support device 10 of FIGS. 1–3 as being used as a cervical collar or brace. As can be seen particularly in FIG. 9, central portion 20, with pad member 30 and deformable sheet means 32 in slot 26 of central portion 20, is positioned against the back of the neck of user 50 to immobilize the spinal region or to restrict the range of motion of the cervical spine of user 50. The deformable sheet means 32 being curved to its predetermined curvature deforms the gel or fluid composition in pad member 30 while the muscle and/or bone of the cervical spine controls to a certain degree the displacement of the gel medium in support device 10. The gel or fluid composition in pad member 30, when displaced by a portion of the anatomy at a single point, is restricted from inordinately moving out of the perimeters of the pad member 30 by inner layer 24 and outer layer 22 of central portion 20.

As an example, the measurements of support device 10 for use around the neck of a human being such as user 50 in FIGS. 8 and 9, may be about ¼ inches thick, 3 inches wide, and 4-½ long. The thickness of deformable sheet means 32 or 42 may range from about ⅛ inches to about ½. The width of deformable sheet means 32 or 42 may measure from about 2 inches to about 8 inches, and its length may measure from about 2 inches to about 8 inches. It is to be appreciated that these dimensions may change when used on other parts of the human body or when used on other members of the animal kingdom.

When support device 10 of FIGS. 7–9 is used as a cervical brace it may employ an occipital support means 52 and a chin support means 54, as best shown in FIG. 7.

Occipital support means 52 and chin support means 54 each has a rest plate member 56 and 58, respectively, with a resilient pad member indicated at numerals 60, 62, respectively, as shown best in FIG. 7 and may generally be constructed similar to that disclosed in the aforementioned U.S. Pat. No. 5,141,489 which is incorporated herein by reference. Resilient pad member 60, 62 may be constructed similarly to that discussed with reference to pad member 30 of the support device 10 of the present invention or which may be constructed similarly to that disclosed in U.S. Pat. No. 5,141,489.

Referring particularly to FIG. 7, support device 10 further comprises a slot 56 formed on an inner surface of connecting end 12 opposite to the outer surface containing the hook and loop means 13 of end 12 as shown in FIG. 1.

Still referring particularly to FIG. 7, chin support means 54 has a post member 64 which slides into slot 56 in connecting end 12 of support device 10 for supporting the chin as best shown in FIG. 8. Occipital support means 52 has a post 66 with curved prongs 68 and 70 which fit down over curved member 36 of deformable sheet means 32 for support of occipital support means 52 by deformable sheet means 32, as particularly shown in FIG. 9. Even though prongs 68 and 70 are shown in FIG. 7, it is to be appreciated that alternate means may be used for mounting occipital support means 52 to deformable sheet means 32 such as providing a bayonet fit between post 66 of occipital support means 52 and deformable sheet means 32. Also, occipital support means may contain a post similar to post member 64 of chin support means 54 which may be received in a slot formed on outer layer 22 or which may be wedged between pad member 30 and deformable sheet means 32, or which may be supported in slots provided in deformable sheet means 32.

The support device 10 of FIGS. 7–9 with its optional components 52 and 54 may be assembled and secured to user 50 in an appropriate manner according to the expertise of the medical professional. As discussed hereinabove, chin and occipital supports 52, 54 are easily removed and inserted into support device 10 and their length may vary in order to be consistent with and to stabilize the postural adjustment of deformable means 32.

The combination of the pad members 60, 62 in supports 52 and 54, respectively, and pad member 30 of support device 10 of FIGS. 7–9 provide optimum comfort to user 50 while adequately bracing or immobilizing the head of user 50.

From the above it is apparent that the support device 10 of FIGS. 1–9 can be used as a support around a non-articulated area of a user to relieve muscle and/or bone strain or soreness as shown in FIG. 6 or with reference to FIGS. 7–9, it can be used to immobilize or restrict movement of an articulated area or joint, such as a cervical spine, where it serves as a cervical collar without components 52, 54 or where it can optionally be used as a cervical brace employing components 52, 54 of these FIGS. 7–9.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described and certain features may be used independently of other features without departing from the spirit or scope of the invention as defined in the appended claims.

What is claimed is:

1. A method of positioning a support device around an area of a user, the steps comprising:
   providing a resilient pad member responsive to movement by the user having a viscous substance means contained in a flexible member with connecting end portions and a central portion with first slot means, wherein said viscous substance means is provided in said central portion of said flexible member,
   providing permanently deformable means insertable in said first slot means of said central portion of said flexible member adjacent to and in influential contact with said viscous substance means and positionable remote from said area of the user,
   selectively positioning said permanently deformable means to a predetermined shape,
   inserting said selectively positioned deformable means into said central portion of said flexible member adjacent to said viscous substance means to cause said viscous substance means to deform, and
   securing said flexible member around said area of the user to position said viscous substance means adjacent said area of the user and said deformable means remote from said area of the user, wherein said viscous substance means positions the anatomy of the user in a particular posture while providing the required support and comfort to the user.

2. A method of claim 1 wherein said forming of said permanently deformable means is performed in situ.

3. A method of positioning a support device around an area of a user, the steps comprising:
   providing a flexible member with connecting end portions and a central portion with first slot means,
   providing viscous substance means in said central portion of said flexible member,
   providing permanently deformable means insertable in said first slot means of said central portion of said flexible member adjacent to said viscous substance means,
   forming said permanently deformable means to a predetermined shape,
   inserting said deformable means into said central portion of said flexible member adjacent to said viscous substance means to cause said viscous substance means to deform, and
   securing said flexible member around said area of the user to position said viscous substance means adjacent said area of the user and said deformable means remote from said area of the user wherein said viscous substance means conforms to the shape of the anatomy around said area to provide the required optimum support and optimum comfort to the user, wherein the user is a human being and the steps further comprising:
   using said support device as a cervical collar which includes the step of arranging said flexible member around the neck of the user such that said deformable means acts upon the cervical spine of the user.

4. A method of claim 3 the steps further comprising:

providing second slot means in said flexible member to receive and support chin support means, and using said deformable means to support occipital support means for use of said support device as a cervical brace.

5. A method of positioning a support device around an area of a user, the steps comprising:

providing a resilient pad member responsive to movement by the user having a viscous substance means contained in a flexible member with connected end portions and a central portion with first slot means wherein said viscous substance means is provided in said central portion of said flexible member, providing permanently deformable means, securing said flexible member around said area of the user while placing said viscous substance means adjacent to said area of the user, selectively positioning said permanently deformable means to a predetermined shape, and inserting said selectively positioned deformable means into said central portion of said flexible member adjacent to said viscous substance means and remote from said area of the user to cause said viscous substance means to position the anatomy of the user in a particular posture to provide the required support and comfort to the user.

6. A method of claim 5 wherein said forming of said permanently deformable means is done in situ.

7. A method of positioning a support device around an area of a user, the steps comprising:

providing a flexible member with connected end portions and a central portion with first slot means, providing viscous substance means in said central portion of said flexible member, providing permanently deformable means, securing said flexible member around said area of the user while placing said viscous substance means adjacent to said area of the user, forming said permanently deformable means to a predetermined shape, and inserting said deformable means into said central portion of said flexible member adjacent to said viscous substance means and remote from said area of the user to cause said viscous substance means to deform and to conform to the shape of said area to provide the required optimum support and optimum comfort to the user, wherein the user is a human being and the steps further comprising:

using said support device as a cervical collar which includes the step of arranging said flexible member around the neck of the user such that said deformable means acts upon the cervical spine of the user.

8. A method of claim 7 the steps further comprising:

providing second slot means in said flexible member to receive and support chin support means, and using said deformable means to support occipital support means for use of said support device as a cervical brace.

9. A method of supporting a non-articulated or an articulated area of the anatomy of a user, the steps comprising:

securing a flexible member around said area of the user, providing viscous substance means in said flexible member adjacent said area of the user wherein said flexible member has a central portion and said viscous substance means is provided in said central portion, selectively positioning in situ said permanently deformable means to a desired predetermined shape, and inserting said deformable means in said flexible member adjacent to said viscous substance means and remote from said area of the user to conform said viscous substance means to said predetermined shape thereby positioning the anatomy of the user in a particular posture to provide comfort to the user and a desired amount of support to said area.

10. A method of supporting a non-articulated or an articulated area of the anatomy of a user, the steps comprising:

securing a flexible member around said area of the user, providing viscous substance means in said flexible member adjacent said area of the user, deforming in situ permanently deformable means to a desired degree, and inserting said deformable means in said flexible member adjacent to said viscous substance means and remote from said area of the user to conform said viscous substance means to a predetermined shape to provide comfort to the user and a desired amount of support to said area wherein said user is a human being and the steps further comprising:

using said support device as a cervical collar which includes the step of arranging said flexible member around the neck of the user such that said deformable means acts upon the cervical spine of the user.

11. A method of claim 10 the steps further comprising:

providing slot means in said flexible member to receive and support chin support means, and using said deformable means to support occipital support means for use of said support device as a cervical brace.

* * * * *